United States Patent
Haraguchi

(10) Patent No.: US 9,924,918 B2
(45) Date of Patent: Mar. 27, 2018

(54) CONTROL APPARATUS, CONTROL METHOD, AND STORAGE MEDIUM

(71) Applicant: CANON KABUSHIKI KAISHA, Tokyo (JP)

(72) Inventor: Tomohiko Haraguchi, Kawasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 248 days.

(21) Appl. No.: 15/044,603

(22) Filed: Feb. 16, 2016

(65) Prior Publication Data
US 2016/0249876 A1    Sep. 1, 2016

(30) Foreign Application Priority Data
Feb. 26, 2015 (JP) ................. 2015-037315

(51) Int. Cl.
G06K 9/00 (2006.01)
A61B 6/00 (2006.01)

(52) U.S. Cl.
CPC .............. *A61B 6/542* (2013.01); *A61B 6/548* (2013.01); *A61B 6/566* (2013.01)

(58) Field of Classification Search
CPC ... A61B 6/4007; A61B 6/4014; A61B 8/4472; H01J 37/04
See application file for complete search history.

(56) References Cited

U.S. PATENT DOCUMENTS 6,504,897 B1   1/2003   Yonekawa
2013/0329860 A1*  12/2013  Nonaka ............... A61B 6/4494
378/91

FOREIGN PATENT DOCUMENTS

JP    3893827 B2    3/2007
JP    2009-279055 A    12/2009
JP    2011-206068 A    10/2011

* cited by examiner

*Primary Examiner* — Don Wong
(74) *Attorney, Agent, or Firm* — Fitzpatrick, Cella, Harper & Scinto

(57) ABSTRACT

To improve use convenience to the user who executes imaging work in an imaging environment where plural X-ray generating apparatuses exist, a control apparatus for controlling X-ray irradiations performed by the plural X-ray generating apparatuses has: an obtaining unit for obtaining identification information for uniquely identifying one X-ray generating unit of the plural X-ray generating units, which is specified as a control target which is allowed to emit X-rays; and a control unit for, based on the obtained identification information, controlling so that, for a period of time during which the one X-ray generating unit is specified as the control target, processes regarding the X-ray irradiations by the other X-ray generating units are restricted.

12 Claims, 7 Drawing Sheets

FIG. 6

| X-IF Configuration Tool | | | | |
|---|---|---|---|---|
| UPDATE X-IF INFORMATION | | | | |
| UNIQUE NAME | PATIENT POSITION | IP ADDRESS | CHANNEL ID | |
| GEN1_Channel1 | STANDING | 192.168.100.97 | 1 | |
| GEN1_Channel2 | SUPINE | 192.168.100.97 | 2 | |
| GEN2_Channel1 | CASSETTE | 192.168.100.97 | 3 | |
| | | | | |

OK    Cancel

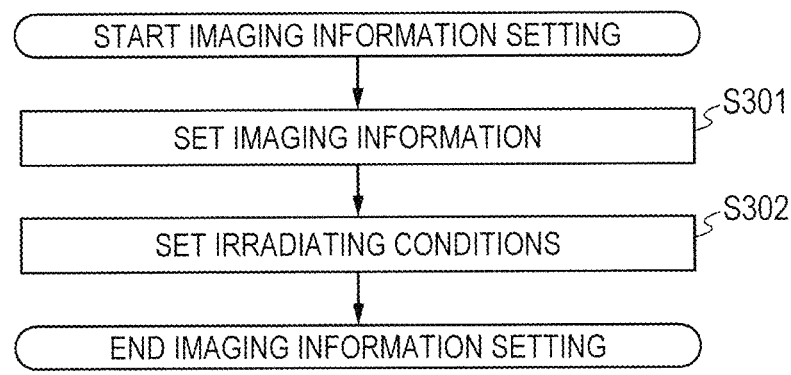
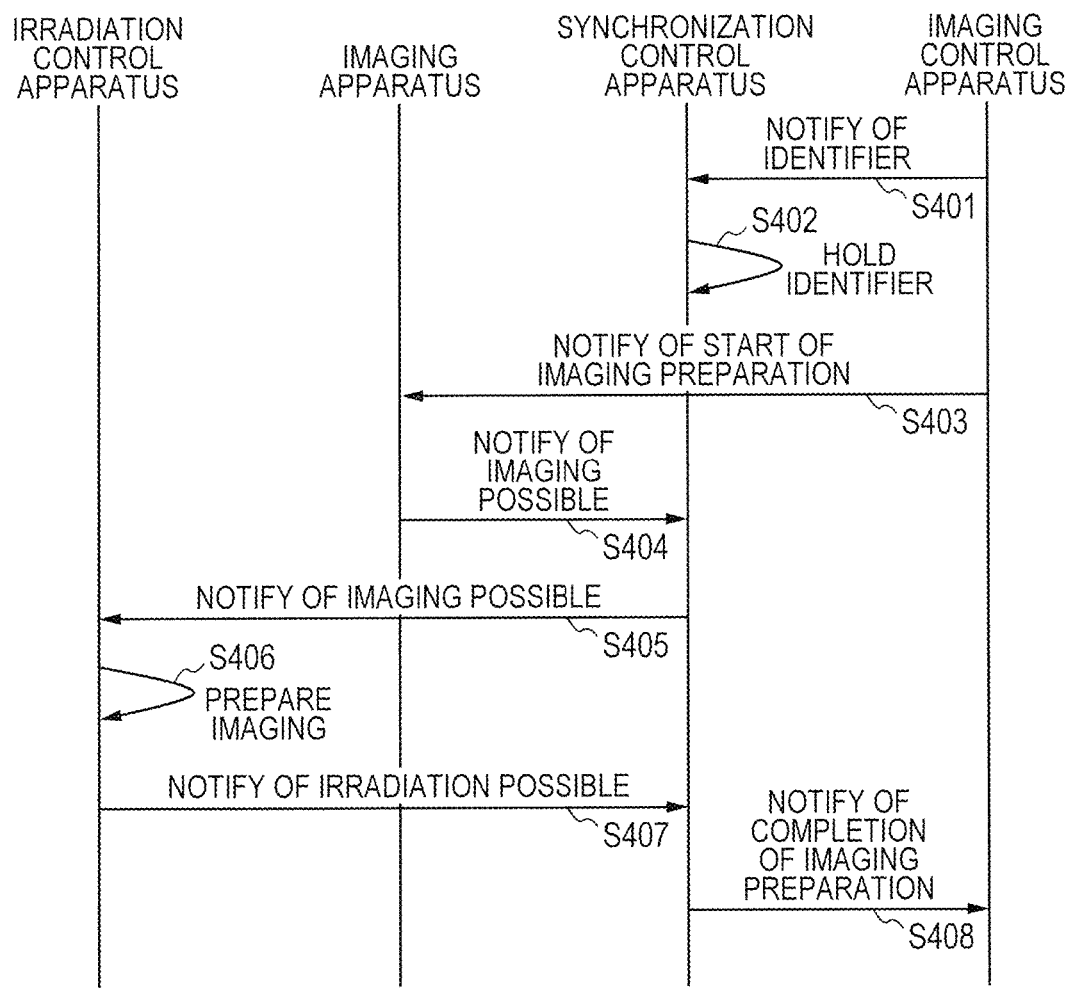

CONTROL APPARATUS, CONTROL METHOD, AND STORAGE MEDIUM

BACKGROUND OF THE INVENTION

Field of the Invention

The present invention relates to a control apparatus, a control method, and a storage medium.

Description of the Related Art

In recent years, in an X-ray imaging diagnosis, an imaging apparatus for an X-ray imaging for obtaining an X-ray image as digital data (hereinbelow, referred to as an X-ray imaging apparatus) is a main stream. There are a variety of imaging scenes in association with the realization of a variety of X-ray imaging apparatuses. Particularly, a portable X-ray imaging apparatus suitable for a movement in an imaging room, a round of visits in a hospital, or the like is widely used. In association with a spread of the portable X-ray imaging apparatuses, the number of such situations that plural X-ray generating apparatuses are installed in the imaging room, a single X-ray generating apparatus having plural X-ray tubes is used, and the like is increasing.

For example, in the case where the user selects the X-ray tube which is used for the imaging from plural X-ray tubes and images, it is required that the proper X-ray tube can be simply and easily selected. Naturally, if an X-ray was irradiated from the X-ray tube which the user does not intend, a proper diagnosis image cannot be imaged and the patient is subjected to a wasteful radiation exposure. To solve such problems, the following techniques have been disclosed.

According to the technique disclosed in Japanese Patent No. 3893827, plural X-ray tubes and plural portable X-ray imaging apparatuses are previously associated with each other and when the user selects one of the associated X-ray tube and portable X-ray imaging apparatus, the other one is also automatically selected. Thus, the X-ray tube can be easily selected and the imaging cannot be performed by using the apparatuses other than the preset associated X-ray tube and portable X-ray imaging apparatus.

According to the technique disclosed in Japanese Patent Application Laid-Open No. 2009-279055, in an imaging system in which an X-ray imaging apparatus is installed in a bucky apparatus and a imaging is performed, an X-ray generating apparatus and the bucky apparatus are previously associated with each other. When the X-ray imaging apparatus is installed in the bucky apparatus, an X-ray irradiation from the X-ray generating apparatus corresponding to the installed bucky apparatus can be performed.

According to the technique disclosed in Japanese Patent Application Laid-Open No. 2011-206068, a switch to designate an X-ray tube is provided for an X-ray imaging apparatus and, by switching the switch by the user, the X-ray tube which is used for imaging is switched.

However, according to the techniques disclosed in Japanese Patent No. 3893827 and Japanese Patent Application Laid-Open No. 2009-279055, it is assumed as a prerequisite that the association (or correspondence) between the X-ray imaging apparatus or the bucky apparatus and the X-ray generating apparatus has been predetermined, and nothing is considered about a point that the association is switched during the imaging. Therefore, there is such a problem that the user cannot easily change the association during the imaging work.

According to the technique disclosed in Japanese Patent Application Laid-Open No. 2011-206068, although the setting and switching of the X-ray tube corresponding to the X-ray imaging apparatus can be simply performed by the switch provided for the X-ray imaging apparatus, since a switch construction or the like is subjected to a restriction of hardware, there is such a problem that the setting and a switching method are complicated. In order to reduce a possibility that the user is subjected to a radiation exposure, generally, devices such as an irradiation switch for controlling the imaging and the like and the X-ray imaging apparatus are away from each other by a predetermined distance. Therefore, if the X-ray imaging apparatus has the switch, there is such a problem that each time the X-ray tube is switched, the user needs to move to the installing location of the X-ray imaging apparatus and it results in a burden to the user.

As mentioned above, according to the techniques in the related arts, there is such a problem that, in an imaging environment where plural X-ray generating apparatuses exist, when the generation of the X-ray from the apparatus which the user does not intend is suppressed, a use convenience to the user who performs the imaging work is low.

It is, therefore, an aspect of the invention to improve a use convenience to the user who performs the imaging work in an imaging environment where plural X-ray generating apparatuses exist.

SUMMARY OF THE INVENTION

According to an aspect of the invention, therefore, there is provided a control apparatus for controlling X-ray irradiations which are performed by plural X-ray generating units, comprising: an obtaining unit configured to obtain identification information for uniquely identifying one X-ray generating unit of the plural X-ray generating units, which is specified as a control target which is allowed to emit X-rays; and a control unit configured to, based on the obtained identification information, control in such a manner that, for a period of time during which the one X-ray generating unit is specified as the control target, processes regarding the X-ray irradiations by the other X-ray generating units are restricted.

According to the aspect of the invention, in the imaging environment where plural X-ray generating apparatuses exist, the use convenience to the user who performs the imaging work can be improved.

Further features of the present invention will become apparent from the following description of exemplary embodiments with reference to the attached drawings.

BRIEF DESCRIPTION OF THE DRAWINGS

FIG. 2 is a diagram illustrating an example of a hardware construction such as an imaging control apparatus and the like.

FIG. 6 is a diagram illustrating an example of an association setting screen for associating an irradiating apparatus with position information of the patient.

FIG. 7 is a flowchart illustrating an example of a process regarding a setting of imaging information.

FIG. 8 is a sequence diagram illustrating an example of an imaging process.

DESCRIPTION OF THE EMBODIMENTS

Preferred embodiments of the present invention will now be described in detail in accordance with the accompanying drawings.

Embodiment 1

Figure 1:
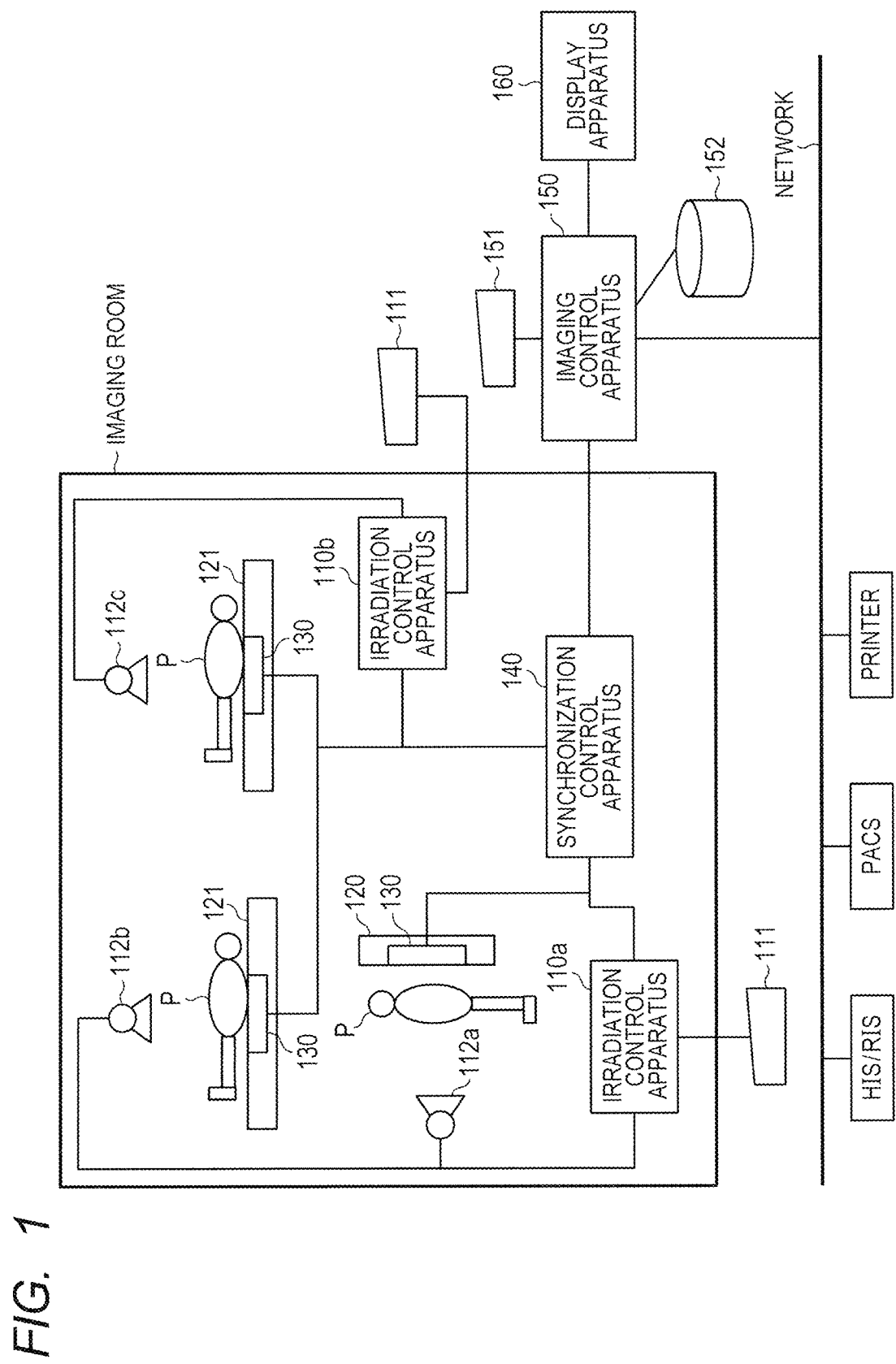
FIG. 1 is a diagram illustrating an example of a system construction in an embodiment 1.

FIG. 1 is a diagram illustrating an example of a system construction of an X-ray imaging system in an embodiment. The X-ray imaging system in the embodiment includes: an irradiation control apparatus 110 for controlling an irradiation of an X-ray (in the example of FIG. 1, an irradiation control apparatus 110a and an irradiation control apparatus 110b); an irradiation inputting apparatus 111 for receiving an input of irradiating conditions of the X-ray, which will be described hereinafter, and an input of start/end of the X-ray irradiation; and an irradiating apparatus 112 for irradiating an X-ray. The irradiating apparatus 112 mentioned here is an example of an X-ray generating unit and is, for example, an X-ray tube or the like. The X-ray imaging system also includes: a fixing apparatus 120 (of an imaging apparatus for a standing position) for installing an imaging apparatus 130 at the time of imaging at a standing position; a fixing apparatus 121 (of an imaging apparatus for a supine position) for installing the imaging apparatus 130 at the time of imaging at a supine position; and the imaging apparatus 130 for reading the irradiated X-ray and generating image data. The X-ray imaging system also includes: a synchronization control apparatus 140 for controlling the irradiation control apparatus 110 and the imaging apparatus 130 synchronously with each other; an imaging control apparatus 150 for controlling the whole imaging; and an imaging information inputting apparatus 151 for receiving an input such as imaging information and the like, which will be described hereinafter. The X-ray imaging system further includes: an imaging information managing apparatus 152 for managing and storing set imaging information and the like; and a display apparatus 160 for displaying the imaging information and image data and presenting to the user.

In FIG. 1, a portion where the apparatuses are connected by a line is a portion where a transmission and a reception of data occur by communication. At this time, a communication medium such as wired communication, wireless communication, or the like, a communication protocol, and the like are not limited. The X-ray imaging system in the embodiment is a system which presumes an X-ray imaging which is performed in a hospital or the like and, generally, presumes a case where plural irradiation control apparatuses 110 and plural irradiating apparatuses 112 exist in an imaging room for X-ray imaging. As mentioned above, in the example of FIG. 1, the irradiation control apparatus 110a and the irradiation control apparatus 110b are installed, the irradiation control apparatus 110a has two irradiating apparatuses 112a and 112b, and the irradiation control apparatus 110b has one irradiating apparatus 112c. However, the numbers of those apparatuses are not limited to the numbers shown in the example of FIG. 1. Although the embodiment will be described on the assumption that the irradiation control apparatus 110, imaging apparatus 130, synchronization control apparatus 140, and imaging control apparatus 150 are independent apparatuses, a part or all of them may be constructed by the same apparatus (control apparatus).

Figure 2:
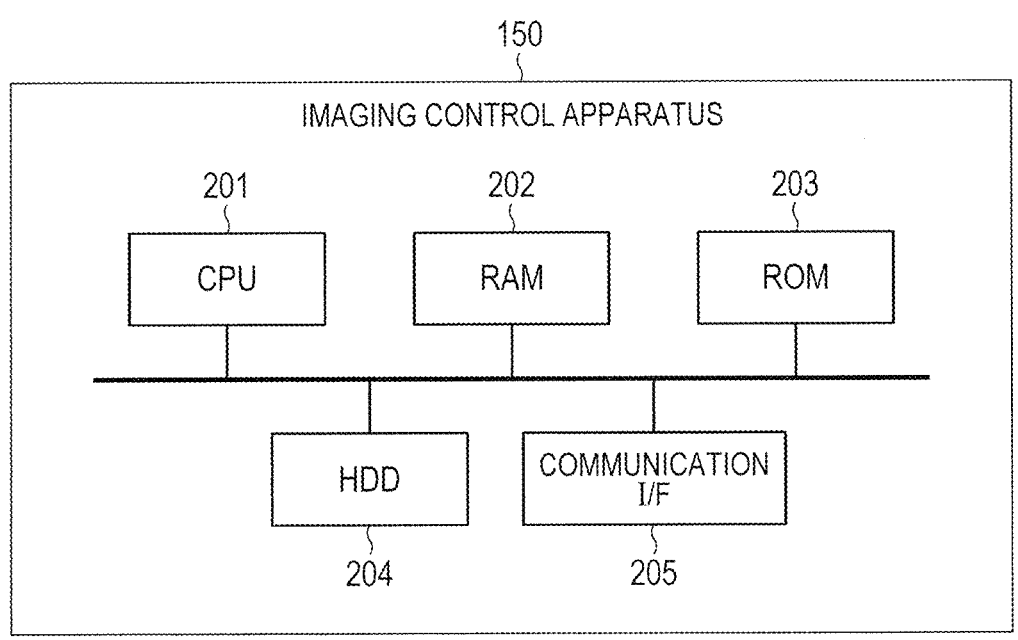

FIG. 2 is a diagram illustrating an example of a hardware construction of the imaging control apparatus 150. The imaging control apparatus 150 has a CPU 201, a RAM 202, a ROM 203, an HDD 204, and a communication I/F 205. The CPU 201 unitedly controls the operation of the imaging control apparatus 150. The RAM 202 functions as a main memory, a work area, or the like of the CPU 201. A program necessary for the CPU 201 to execute the processes and the like have been stored in the ROM 203. The program may be stored in the HDD 204. The CPU 201 loads the necessary program from the ROM 203 or the like into the RAM 202 and executes, thereby realizing the function of the imaging control apparatus 150 and the processes of the imaging control apparatus 150 shown in flowcharts and sequence diagrams, which will be described hereinafter. The communication I/F 205 communicates with the outside of the imaging control apparatus 150.

It is now assumed that an outline of a hardware construction of the irradiation control apparatus 110, imaging apparatus 130, and synchronization control apparatus 140 is also similar to that illustrated in FIG. 2. Functions and the like of the respective apparatuses will be described hereinbelow also with reference to a more specific hardware construction.

The irradiation control apparatus 110 is constructed by a microprocessor or the like in which a control driving program has been stored and controls a high voltage generating apparatus (not shown) on the basis of irradiating conditions set by the irradiation inputting apparatus 111. The high voltage generating apparatus generates a high voltage and applies to the irradiating apparatus 112, so that an X-ray is irradiated. The irradiating conditions mentioned here denote an identifier (identification information) for uniquely identifying the irradiating apparatus (X-ray tube) 112 and a tube voltage, a tube current, an irradiating time, and the like of the irradiating apparatus 112. As a control system, there is a single phase transformer system, an inverter system, a capacitor system, or the like. An output system differs depending on the control system. However, the control system in the embodiment is not limited to those control systems.

The irradiating apparatus 112 is constructed by a filament, a coil, a target, and the like. An electron beam generated by the high voltage collides with a target, so that an X-ray is generated. The irradiation inputting apparatus 111 is a console or the like on which a touch panel display and various kinds of buttons are mainly arranged. A setting value of each irradiating condition is displayed on a display. The setting value can be changed or the like by a button operation. The apparatus may have such a construction that dedicated irradiation switches for notifying the user of the start/end of the irradiation are provided. In this case, there is considered such a construction that the X-ray is irradiated for a period of time during which the user is depressing the switch and the irradiation is finished when the user releases the switch.

The fixing apparatus 120 of the imaging apparatus for the standing position is an apparatus to perform the imaging in a state where an object (patient) P to be imaged is standing. The fixing apparatus 120 is constructed by: a unit for installing the imaging apparatus 130; and a moving unit for elevating such a unit upward or downward. Thus, the imaging apparatus 130 can be disposed at a proper position in accordance with a physique and an imaging region of the object P. The fixing apparatus 121 of the imaging apparatus for the supine position is an apparatus to perform the imaging in a state where the object P lies down. The fixing apparatus 121 is constructed by: a unit for installing the imaging apparatus 130; and a moving unit for moving such a unit in parallel. Thus, the imaging apparatus 130 can be disposed at a proper position in accordance with a physique and an imaging region of the object P.

The imaging apparatus 130 is constructed by: a multiprocessor unit for controlling the driving of the imaging apparatus 130; a capacitor for reading the X-ray; a TFT (Thin Film Transistor) switch; a charge amplifier; and the like. The imaging apparatus 130 converts energy of the X-ray irradiated from the irradiating apparatus 112 into an electric signal, constructs image data, and transmits to the imaging apparatus 130. More specifically describing, the imaging apparatus 130 converts the energy of the X-ray received from the irradiating apparatus 112 into an amount of charges. The charges are accumulated into capacitors of pixels arranged in a matrix form. The accumulated charges are A/D converted by the charge amplifier through the TFT switch and are read out as digital values. The TFT switch is a semiconductor element whose switching operation is performed by a thin film transistor. The TFT switch reads the pixels of the whole display screen by such a scan that the ON/OFF operations of the TFT switch are switched every row, thereby obtaining the X-ray image data. A preset driving program is switched and controlled by the multiprocessor unit in accordance with a state of the imaging apparatus 130. For example, in a standby state, control is made so as to perform such an idling driving that the charges accumulated in the capacitors are refreshed and pixel information is read. In a during-imaging state, control is made so as to perform such a reading driving that the charges are accumulated for a predetermined time, the charge amplifier is energized, and thereafter, the image information is read.

The synchronization control apparatus 140 is constructed by a control board comprising: a microprocessor; a memory; a communication interface; and the like. The synchronization control apparatus 140 operates in such a manner that information of the irradiation control apparatus 110, imaging apparatus 130, and imaging control apparatus 150 serving as communication targets is held in a memory and a synchronization among the apparatuses is attained at the time of imaging. More specifically describing, the synchronization control apparatus 140 obtains and holds an identifier of the irradiating apparatus 112 which has been preset by the user, discriminates whether or not the identifier is a signal added with such an identifier, and processes only the relevant signal. A more detailed description will be made hereinafter with reference to FIG. 8 and the like.

The imaging control apparatus 150 manages and controls a state of the whole system. Generally, the imaging control apparatus 150 is a computer of a desk-top type, a notebook type, or a tablet type. The imaging control apparatus 150 has a communication interface and is connected to an external apparatus network. The imaging control apparatus 150 is mainly connected to an HIS (Hospital Information System) and an RIS (Radiation Information System) in a hospital and can also obtain patient information in an on-line manner. Further, the imaging control apparatus 150 is connected to a PACS (Picture Archiving and Communication System) and can also hold imaging image data or the like into a dedicated server connected to the external apparatus network.

The imaging information inputting apparatus 151 is an inputting apparatus such as touch panel display, mouse, keyboard, or the like. The user can set imaging information regarding the imaging through the operation of the imaging information inputting apparatus 151 and can set setting information regarding the setting of the system and the like.

The imaging information mentioned here is information including: patient information of the patient serving as an object of the X-ray imaging; position information of the patient; imaging region information of the patient; type information of the imaging apparatus 130; disposing information showing a disposing situation of the imaging apparatus 130; and the like. The patient information is information showing a name, sex, age, and the like of the patient. The position information is information showing a position (posture) of the patient such as standing position, supine position, cassette (portable), and the like. The imaging information can be also input by using the imaging information inputting apparatus 151 or can be also input by obtaining imaging information from the HIS or RIS in the foregoing external apparatus network. It is also possible to use such a construction that a bar code storing the patient information is printed onto a chart or the like of the patient and the bar code is read by using a bar code reader, thereby obtaining and inputting the imaging information. Further, it is also possible to use such a construction that the patient information is stored into a magnetic card, an IC card, or the like and is read by using a bar code reader, thereby obtaining and inputting the imaging information.

The imaging information managing apparatus 152 is constructed by a magnetic storage device such as a hard disk or the like or by an SSD (Solid-State Drive) such as a storage device of a large capacity using a semiconductor memory. The imaging information managing apparatus 152 stores the imaging information designated by the imaging information inputting apparatus 151, various kinds of setting information, various kinds of definition information, imaging image data, and the like. Since it is actually difficult to hold all data, generally, the data is transferred to the foregoing PACS or the like and is managed. The display apparatus 160 displays the imaging information, the image data after the imaging, and the like and notifies the user of them. As a display apparatus 160, a normal display which does not accept the touch operation may be used or a touch panel display may be used in order to attach importance to the operability.

Figure 3:
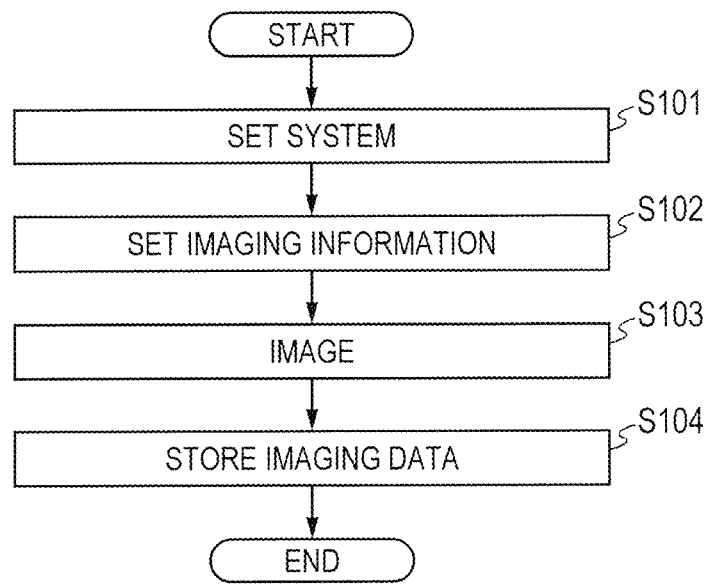
FIG. 3 is a flowchart illustrating an example of an outline of processes in the embodiment 1.

Subsequently, a processing flow in the X-ray imaging system in the embodiment will be described. FIG. 3 is a flowchart illustrating an example of an outline of a process in the embodiment. In S101, the imaging control apparatus 150 stores the setting information regarding and the definition information regarding the system setting set through the operation of the imaging information inputting apparatus 151 into the imaging information managing apparatus 152. The process in S101 will be described in detail hereinafter with reference to FIG. 4 and the like. The setting information mentioned here is information regarding a communication setting or the like for allowing the irradiation control apparatus 110, imaging apparatus 130, and the like to communicate with the imaging control apparatus 150. The definition information mentioned here is information regarding a definition and the like of the position shown by the position information of the patient.

In S102, the imaging control apparatus 150 stores the imaging information set through the operation of the imaging information inputting apparatus 151 into the imaging information managing apparatus 152. The imaging control apparatus 150 stores the setting information of the irradiating conditions set through the operation of the irradiation inputting apparatus 111 into the imaging information managing apparatus 152. The process in S102 will be described in detail hereinafter with reference to FIG. 7 and the like. In S103, the imaging control apparatus 150 starts the X-ray imaging. In S104, the imaging control apparatus 150 stores the image data after the imaging into the imaging information managing apparatus 152 in association with the imaging information set in S102. The above description is an outline of the processing flow in the X-ray imaging system in the embodiment.

Figure 4:
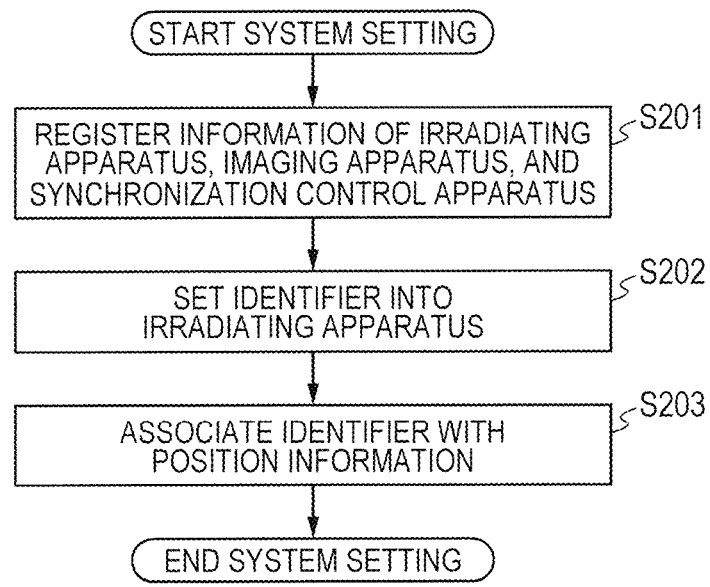
FIG. 4 is a flowchart illustrating an example of a process regarding a system setting.
Figure 5:
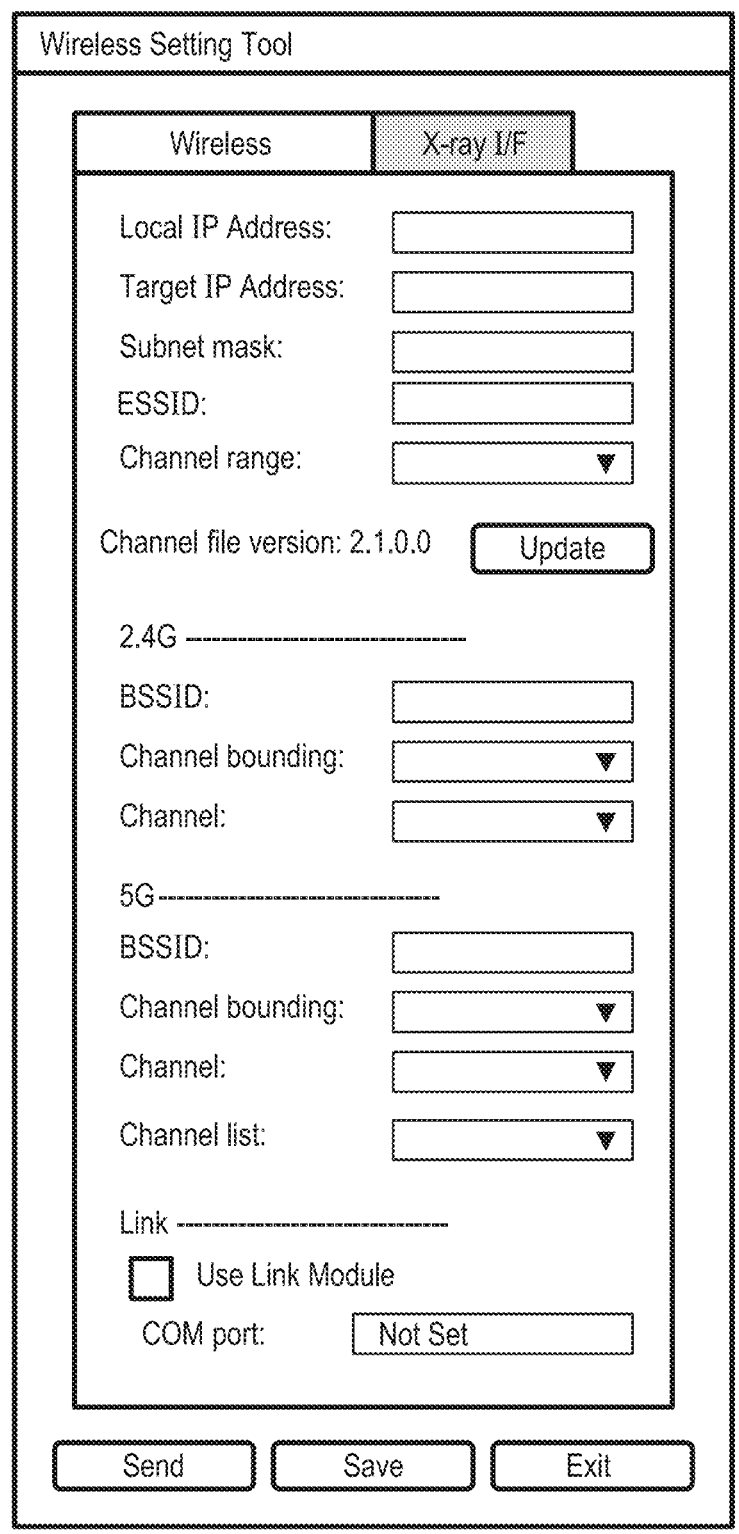
FIG. 5 is a diagram illustrating an example of a setting screen for the system setting.

Subsequently, the process (S101) regarding the system setting in FIG. 3 will be described in detail with reference to FIG. 4. FIG. 4 is a flowchart illustrating an example of the process regarding the system setting in S101 in FIG. 3. In S201, the imaging control apparatus 150 stores the setting information for allowing each apparatus set through the operation of the imaging information inputting apparatus 151 to communicate into the imaging information managing apparatus 152. In more details, a user interface for inputting information necessary for communication such as IP address, subnet mask, and the like of each apparatus as illustrated in FIG. 5 is prepared for the display apparatus 160. FIG. 5 is a diagram illustrating an example of the setting screen in the system setting. The user inputs the IP addresses, subnet masks, and the like of the irradiation control apparatus 110, imaging apparatus 130, and synchronization control apparatus 140 from the imaging information inputting apparatus 151. The imaging control apparatus 150 discriminates whether or not the input value as setting information which was input is proper or the like, and stores a discrimination result into the imaging information managing apparatus 152.

In S202, the imaging control apparatus 150 receives and sets, through the imaging information inputting apparatus 151, the input of the identifier which has been registered in S201 and is allocated to each irradiating apparatus 112 connected to the irradiation control apparatus 110. In S203, the imaging control apparatus 150 associates the identifier set for each irradiating apparatus 112 in S202 with the position information which was input through the imaging information inputting apparatus 151 and generates association information. At this time, the imaging control apparatus 150 receives an associating instruction through a setting screen illustrated in FIG. 6. FIG. 6 is a diagram illustrating an example of the association setting screen for associating each irradiating apparatus 112 with the position information of the patient. A case of setting a unique name as an identifier is shown. Therefore, for example, each irradiating apparatus 112 and the position information of the patient are associated in such a manner that when the patient is in a standing position, the irradiating apparatus 112a is used, when the patient is in a supine position, the irradiating apparatus 112b is used, and the like. Although the information which is associated with the identifier is assumed to be the position information included in the imaging information here, the information which is associated with the identifier may be another information included in the imaging information.

Subsequently, the process (S102) regarding the setting of the imaging information in FIG. 3 will be described in detail with reference to FIG. 7. FIG. 7 is a flowchart illustrating an example of the process regarding the setting of the imaging information in S102 in FIG. 3. In S301, the imaging control apparatus 150 stores the imaging information set through the operation of the imaging information inputting apparatus 151 into the imaging information managing apparatus 152. It is assumed that setting candidates of the imaging information have been predetermined at the time of the system setting. At this time, if such a construction that parameters in which the imaging region and the position of the patient are combined are prepared and, when the user decides one of the parameters of the combinations, the imaging information can be set is used, a use convenience is improved. In the case of associating with the irradiating apparatus 112 by not only the position information but also a combination of the position information and the imaging apparatus 130 or the like, if parameters in which the imaging apparatus 130 is also combined are prepared, the imaging information can be easily set. The imaging control apparatus 150 displays a parameter group prepared for the setting of the imaging information to the display apparatus 160. The user selects various kinds of parameters regarding the setting of the imaging information through the imaging information inputting apparatus 151.

In S302, the imaging control apparatus 150 stores the setting information of the irradiating conditions set through the operation of the irradiation inputting apparatus 111 into the imaging information managing apparatus 152. At this time, as well as S301, the imaging control apparatus 150 displays a parameter group prepared for the setting of the irradiating conditions to the display apparatus 160. The user selects various kinds of parameters regarding the setting of the irradiating conditions through the irradiation inputting apparatus 111.

Subsequently, the imaging processing flow in the X-ray imaging system in the embodiment will be described. FIG. 8 is a sequence diagram illustrating an example of the imaging process in the embodiment.

In S401, the imaging control apparatus 150 decides the irradiating apparatus 112 which is used for the imaging on the basis of the association information stored in the imaging information managing apparatus 152 in S202, and notifies the synchronization control apparatus 140 of the identifier of the decided irradiating apparatus 112. More specifically describing, the imaging control apparatus 150 searches the association information on the basis of the position information designated by the user and obtains the identifier associated with the position information. In this manner, the imaging control apparatus 150 can automatically decide the irradiating apparatus 112 associated with the position information designated by the user. In S402, the synchronization control apparatus 140 holds the notified identifier. For a period of time during which the identifier is held, the synchronization control apparatus 140 processes only the signal from the irradiating apparatus 112 specified by the identifier and does not process the signals from the other irradiating apparatuses 112. That is, the synchronization control apparatus 140 controls so as to restrict the X-ray irradiations from the irradiating apparatuses 112 other than the irradiating apparatus 112 specified by the notified identifier. Consequently, the X-ray irradiation from the irradiating apparatus 112 which the user does not intend can be restricted.

In S403, on the basis of the set imaging information, the imaging control apparatus 150 notifies an imaging preparation start signal to the imaging apparatus 130 which is used in the imaging. In S404, the imaging apparatus 130 which received such a notification executes an imaging preparation driving. After completion of the preparation driving, the imaging apparatus 130 notifies the synchronization control apparatus 140 of an imaging possible signal. In S405, the synchronization control apparatus 140 which received such a notification notifies the imaging possible signal to the irradiation control apparatus 110 specified by the held identifier. At this time, by also allocating the identifier and notifying, it is also possible to cope with a case where plural irradiating apparatuses 112 are connected to the irradiation control apparatus 110. In the case where communication cannot be performed for a predetermined time like a case where the irradiating apparatus 112 which is specified by the identifier held in the synchronization control apparatus 140 does not exist, or the like, the synchronization control apparatus 140 notifies the imaging control apparatus 150 of an error signal and notifies the user of it through the display apparatus 160.

In S406, the irradiation control apparatus 110 which received the imaging possible signal performs preparation control for generating the X-ray. In S407, when the system enters a state where the X-ray can be irradiated, the irradiation control apparatus 110 notifies the synchronization control apparatus 140 of an irradiation possible signal. In S408, the synchronization control apparatus 140 notifies the imaging control apparatus 150 that the imaging apparatus 130 and the irradiation control apparatus 110 entered a imaging possible state.

The imaging control apparatus 150 confirms that the apparatuses entered the imaging possible state, and displays a message showing that the imaging is possible to the display apparatus 160. At this time, the user can also change the association between the position information which has been preset in the preparation before the imaging and the irradiating apparatus 112. When the imaging information is changed after the imaging information was set through the imaging information inputting apparatus 151 and the process shown in FIG. 8 was executed, it is necessary that the irradiating apparatus 112 which is used is changed to the irradiating apparatus 112 corresponding to the position information included in the imaging information after the change. For this purpose, the imaging control apparatus 150 notifies the identifier of the irradiating apparatus 112 after the change to the imaging apparatus 130 and the synchronization control apparatus 140.

Further, in the case of performing plural imaging operations in a lump, a plurality of imaging information can be also preset. At this time, in the case where the association between the position information included in certain imaging information and the identifier of the irradiating apparatus 112 was changed and the same position information also exists in the other irradiating apparatuses 112, the association is similarly changed and the association information may be updated by the imaging control apparatus 150. Thus, such work that the user changes the association can be simplified, and a use convenience can be improved.

Subsequently, the X-ray irradiation is started. The irradiation control apparatus 110 detects that the irradiation start has been instructed by the user from the irradiation inputting apparatus 111, and notifies the synchronization control apparatus 140 of an irradiation permission request signal. The synchronization control apparatus 140 notifies the imaging apparatus 130 of it. The imaging apparatus 130 confirms that it is in an X-ray reading possible state, and returns an irradiation permission signal to the synchronization control apparatus 140. By notifying it to the irradiation control apparatus 110 on a transmission source side, the X-ray is irradiated from the relevant irradiating apparatus 112. At this time, in order to prevent the imaging information from being changed, the synchronization control apparatus 140 notifies the imaging control apparatus 150 of a during-imaging signal showing that the imaging is being performed. The imaging control apparatus 150 which received the during-imaging signal controls in such a manner that the input through the imaging information inputting apparatus 151 is not received.

When the irradiation control apparatus 110 detects that the irradiation end has been instructed from the irradiation inputting apparatus 111, the irradiation control apparatus 110 notifies the synchronization control apparatus 140 of an irradiation end signal. The synchronization control apparatus 140 notifies the imaging apparatus 130 of the irradiation end signal. The imaging apparatus 130 which was notified of the irradiation end signal completes the reading of the X-ray and generates image data. After completion of the generation of the image data, the imaging apparatus 130 transfers the image data to the imaging control apparatus 150. At this time, even if the signal was received from the irradiating apparatus 112 of the identifier different from the identifier of a control target held by the process of S402, the synchronization control apparatus 140 does not process. By controlling in this manner, it is possible to prevent the X-ray from being erroneously irradiated from the irradiating apparatus 112 which the user does not intend.

The imaging control apparatus 150 which received the image data stores the image data into the imaging information managing apparatus 152. At this time, the imaging control apparatus 150 manages the set imaging information and the transferred image data so as to be associated with each other. Thus, the image data can be easily confirmed after the imaging. The imaging control apparatus 150 may also manage the identifier associated with the position information included in the imaging information so as to be associated with the image data. Consequently, whether the image data is image data imaged by the X-ray irradiation from which irradiating apparatus 112 can be easily discriminated.

In the case of shifting to the next imaging, the user sets next imaging information. At this time, it is also possible to construct in such a manner that if the irradiating apparatus 112 which will be used in the next imaging is the same as the irradiating apparatus 112 which was used in the previous imaging, the synchronization control apparatus 140 is not notified of the irradiation end signal.

According to the embodiment as mentioned above, for a period of time during which the identifier of the irradiating apparatus 112 specified as a control target is held, the X-ray irradiation from the irradiating apparatus 112 specified by another identifier can be restricted. Thus, since it is possible to prevent the X-ray from being erroneously irradiated from the irradiating apparatus 112 which the user does not intend, a use convenience to the user who executes the imaging work can be improved. According to the embodiment, by preliminarily managing the position information and the identifier of the irradiating apparatus 112 so as to be associated with each other, the irradiating apparatus 112 which is used can be easily designated or switched and an efficiency of the imaging work can be raised.

Although the case of setting the identifier every irradiating apparatus 112 will be described in the embodiment, the identifier can be set not only every irradiating apparatus 112 but also every irradiation control apparatus 110, every synchronization control apparatus 140, or every interface of the synchronization control apparatus 140.

Although the case of associating the irradiating apparatus 112 with the position information has been described in the embodiment, an association between the irradiation control apparatus 110 and the position information or an association between the synchronization control apparatus 140 and the position information can be also performed. Further, not only the position information but also a combination of the position information and the imaging apparatus 130 is defined as one parameter and they may be associated with the irradiating apparatus 112, irradiation control apparatus 110, or synchronization control apparatus 140. As mentioned above, those information can be managed by a combination which can be easily operated by the user and the embodiment is an example of such a case.

Although the example in which the irradiating apparatus 112 can be automatically designated by designating the position information has been described in the embodiment, the position information can be also automatically specified by designating the irradiating apparatus 112 on the contrary.

Embodiment 2

Since the imaging control apparatus 150 and the irradiation control apparatus 110 do not directly communicate with each in the foregoing embodiment 1, the irradiating conditions cannot be managed by the imaging control apparatus 150. By constructing in such a manner that the imaging control apparatus 150 and the irradiation control apparatus 110 directly communicate with each other, the imaging information and the irradiating conditions can be managed by the imaging control apparatus 150 in association with each other. Therefore, for example, an amount of radiation exposure of each patient or the like can be managed. In the embodiment 2, an example of a construction in which the imaging control apparatus 150 and the irradiation control apparatus 110 directly communicate with each other will be described.

Figure 9:
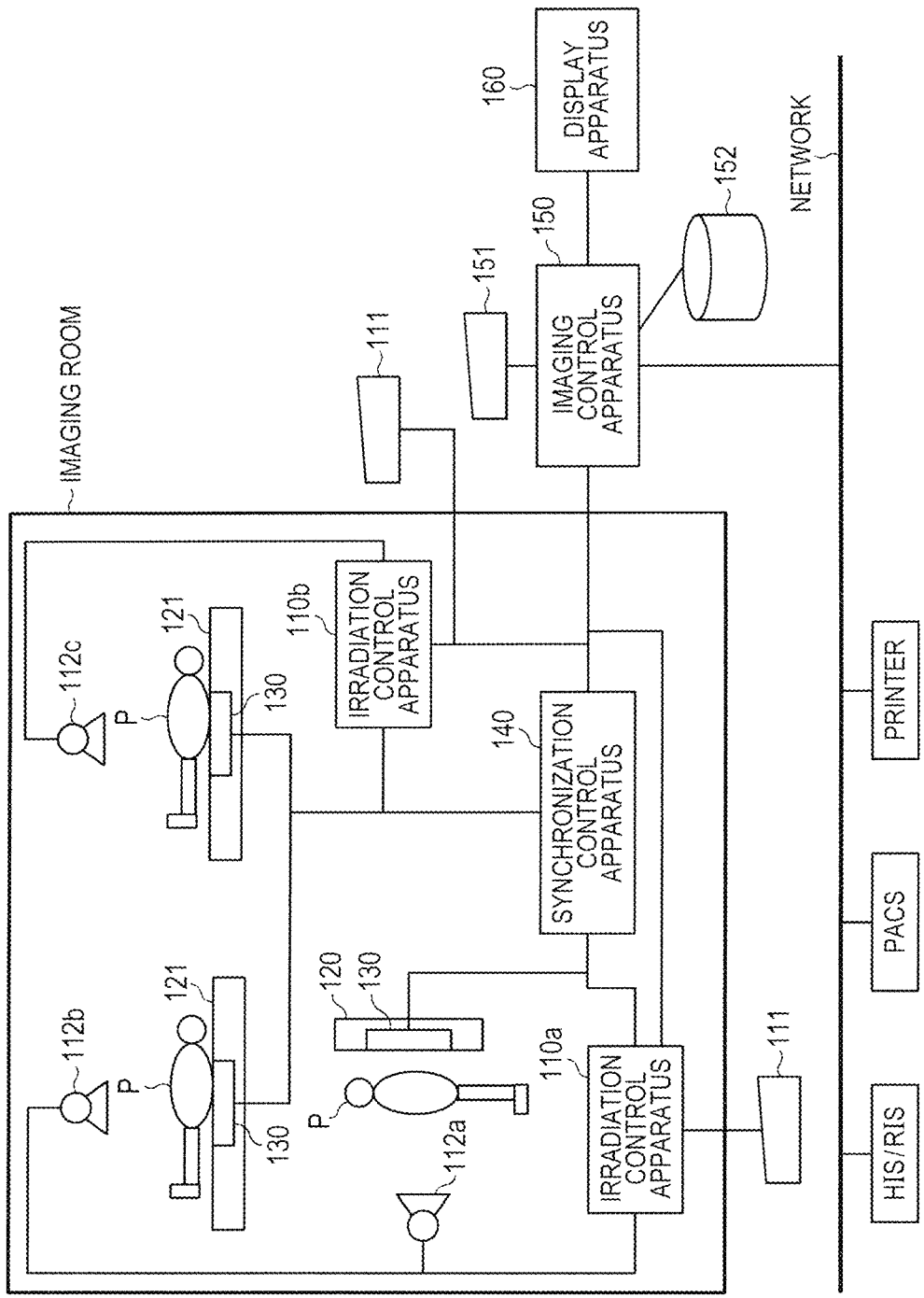
FIG. 9 is a diagram illustrating an example of a system construction in an embodiment 2.

A system construction of an X-ray imaging system in the embodiment 2 is as illustrated in FIG. 9 and its component elements are similar to those in the embodiment 1. The embodiment 2 differs from the embodiment 1 except a point that the imaging control apparatus 150 and the irradiation control apparatus 110 directly communicate with each other.

A processing flow will be described. In S201 in FIG. 4 mentioned above, the imaging control apparatus 150 receives, through the imaging information inputting apparatus 151, an input of the communication setting of the irradiation control apparatus 110 which communicates with the imaging control apparatus 150 and stores setting information regarding the communication setting into the imaging information managing apparatus 152. In S302 in FIG. 7 mentioned above, the irradiation control apparatus 110 notifies the imaging control apparatus 150 of the set irradiating conditions. The imaging control apparatus 150 stores the setting information of the notified irradiating conditions and the imaging information into the imaging information managing apparatus 152 so as to be associated with each other. If the irradiating apparatus 112 associated with the imaging information was changed, the irradiation control apparatus 110 with which the imaging control apparatus 150 communicates is also switched in accordance with such a change. At this time, the irradiation control apparatus 110 notifies the imaging control apparatus 150 of the irradiating conditions set by the irradiation inputting apparatus 111, so that the irradiating conditions which are associated with the imaging information are overwritten and set.

Although the imaging control apparatus 150 starts the communication with the irradiation control apparatus 110 as a communication target at the time of imaging, if the communication cannot be established for a preset period of time or longer, it is determined that the communication is impossible. In such a case, the imaging control apparatus 150 again retries to establish the communication with the set irradiation control apparatus 110. If the communication cannot be established even after the imaging control apparatus 150 executed the retry the predetermined number of times, the communication with the irradiation control apparatus 110 is finished. In such a case, the imaging control apparatus 150 may control so as to disable the imaging. If the synchronization control apparatus 140 can communicate with the irradiation control apparatus 110, the imaging control apparatus 150 may control so as to enable the imaging. In such a case, the imaging control apparatus 150 displays a message showing that the irradiating conditions cannot be obtained to the display apparatus 160, thereby notifying the user of it.

Further, in the case of starting an inspection after a plurality of imaging information were set, such a situation that the irradiation control apparatus 110 which can communicate with the imaging control apparatus 150 and the irradiation control apparatus 110 which cannot communicate with the imaging control apparatus 150 exist mixedly is also considered. In such a case, the imaging control apparatus 150 may control in such a manner that at the time of starting the inspection, the imaging control apparatus 150 previously displays such a fact to the display apparatus 160, thereby notifying the user of it, and the inspection is started, or the imaging is inhibited. Those constructions can be properly set in accordance with an operating method of the user.

According to the embodiment, in the X-ray imaging system in which plural irradiation control apparatuses 110 and plural irradiating apparatuses 112 exist, the imaging control apparatus 150 can communicate the irradiating conditions or the like with the plural irradiation control apparatuses 110. Further, the irradiation control apparatus 110 and the irradiating apparatus 112 which are used for the imaging can be easily switched in accordance with the setting of the user and the imaging can be performed, and an efficiency of the imaging work can be raised.

Other Embodiments

According to the foregoing embodiments as mentioned above, in the imaging environment where plural X-ray generating apparatuses exist, a use convenience to the user who performs the imaging work can be improved.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-037315, filed Feb. 26, 2015, which is hereby incorporated by reference herein in its entirety.

What is claimed is:

1. A control apparatus for controlling X-ray irradiations which are performed by plural X-ray generating units, comprising:
    an obtaining unit configured to obtain identification information for uniquely identifying one X-ray generating unit of the plural X-ray generating units, which is specified as a control target which is allowed to emit X-rays; and
    a control unit configured to, based on the obtained identification information, control in such a manner that, for a period of time during which the one X-ray generating unit is specified as the control target, processes regarding the X-ray irradiations by the other X-ray generating units are restricted.

2. The control apparatus according to claim 1, further comprising a managing unit configured to manage association information in which imaging information regarding an X-ray imaging and the identification information for uniquely identifying the plural X-ray generating units are associated with each other, and
    wherein the obtaining unit obtains identification information obtained by searching the association information managed by the managing unit on the basis of the designated imaging information, as the identification information for uniquely identifying the one X-ray generating unit.

3. The control apparatus according to claim 2, further comprising a first notifying unit configured to notify an error when the identification information associated with the designated imaging information does not exist in the association information managed by the managing unit.

4. The control apparatus according to claim 2, further comprising a second notifying unit configured to notify in such a manner that after the one X-ray generating unit is specified as the control target, if another imaging information is designated, identification information associated with the another imaging information among the identification information included in the association information is notified.

5. The control apparatus according to claim 2, wherein after the one X-ray generating unit is specified as the control target, if another imaging information is designated, the control unit switches communication to the X-ray generating unit of identification information associated with the another imaging information and controls.

6. The control apparatus according to claim 2, wherein if the identification information associated with one imaging information among plural imaging information included in the association information is changed, the managing unit performs the same change also with respect to the same another imaging information as the one imaging information and updates the association information.

7. The control apparatus according to claim 2, wherein the managing unit further manages the imaging information and setting information of an irradiating condition in the X-ray irradiation by the one X-ray generating unit so as to be associated with each other.

8. The control apparatus according to claim 2, further comprising a storing unit configured to associate the designated imaging information with image data obtained by the X-ray imaging according to the control by the control unit and store.

9. The control apparatus according to claim 8, wherein the storing unit further associates the identification information of the X-ray generating unit associated with the imaging information with the image data and stores.

10. The control apparatus according to claim 2, wherein the imaging information is information including at least one of patient information of a patient as an object of the X-ray imaging, position information of the patient, type information of an imaging apparatus for detecting the X-ray irradiation and generating image data, and installing information showing an installing situation of the imaging apparatus.

11. A control method for controlling X-ray irradiations which are performed by plural X-ray generating units, comprising:
    obtaining identification information for uniquely identifying one X-ray generating unit specified as a control target from the plural X-ray generating units;
    controlling, based on the obtained identification information, in such a manner that, for a period of time during which the identification information of the one X-ray generating unit is specified as the control target, processes regarding the X-ray irradiations by the other X-ray generating units are restricted.

12. A non-transitory computer-readable storage medium storing a program for causing a computer, for controlling X-ray irradiations which are performed by plural X-ray generating units, to:
    obtain identification information for uniquely identifying one X-ray generating unit specified as a control target from the plural X-ray generating units;
    control, based on the obtained identification information, in such a manner that, for a period of time during which the identification information of the one X-ray generating unit is specified as the control target, processes regarding the X-ray irradiations by the other X-ray generating units are restricted.

* * * * *